US008942344B2

(12) United States Patent
Klein

(10) Patent No.: US 8,942,344 B2
(45) Date of Patent: Jan. 27, 2015

(54) METHOD FOR DETERMINING THE CONCENTRATION OF AN ELEMENT IN A MATERIAL

(75) Inventor: Albert Klein, Simmersfeld (DE)

(73) Assignee: Elisabeth Katz, Simmersfeld (DE)

( * ) Notice: Subject to any disclaimer, the term of this patent is extended or adjusted under 35 U.S.C. 154(b) by 284 days.

(21) Appl. No.: 13/370,204

(22) Filed: Feb. 9, 2012

(65) Prior Publication Data

US 2013/0208856 A1 Aug. 15, 2013

(51) Int. Cl.
*G01N 23/06* (2006.01)
(52) U.S. Cl.
USPC .......................................................... 378/53
(58) Field of Classification Search
CPC ....... G01N 23/10; G01N 23/12; G01N 23/06; G01N 23/083; A61B 6/482; A61B 6/483
USPC ............................................... 378/51, 53, 54
See application file for complete search history.

(56) References Cited

U.S. PATENT DOCUMENTS

| 5,854,821 A * | 12/1998 | Chase et al. ................... 378/53 |
| 2010/0172470 A1 | 7/2010 | Kuwabara |
| 2010/0303201 A1 | 12/2010 | Klein |

FOREIGN PATENT DOCUMENTS

JP 2002-228603 8/2002

OTHER PUBLICATIONS

Pokrovski et al.:"An in situ X-ray absorption spectroscopy study of gold-chloride complexing in hydrothermal fluids," Chemical Geology, vol. 259, 2009, pp. 17-29.
Shah et al.: "X-Ray Absorption Near Edge Structure Spectrometry Study of Nickel and Lead Speciation in Coals and Coal Combustion Products," Energy & Fuels, vol. 23, 2009, pp. 1518-1525.

* cited by examiner

*Primary Examiner* — Jurie Yun
(74) *Attorney, Agent, or Firm* — Rabin & Berdo, P.C.

(57) ABSTRACT

A method for determining the concentration of an element in a material includes irradiating the material with an X-ray beam having a continuum in the area of an absorption edge of the element to be measured. The intensity of the transmitted X-ray beam is measured with an energy dispersive sensor. The intensity of the transmitted X-ray beam in an energy interval above the absorption edge and in an energy interval below the absorption edge is determined. The concentration of the element is computed on the basis of said intensities.

18 Claims, 4 Drawing Sheets

METHOD FOR DETERMINING THE CONCENTRATION OF AN ELEMENT IN A MATERIAL

Figure 1:
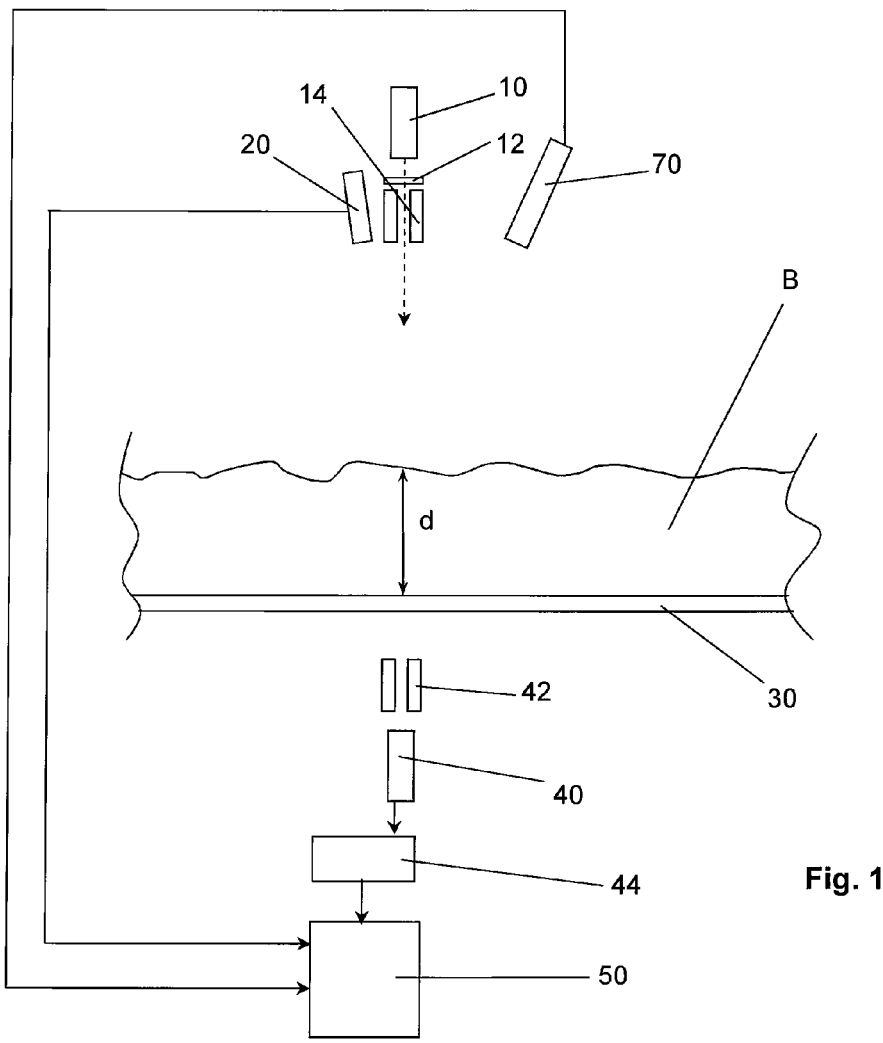

The invention relates to a method for determining the concentration of at least one element in a material.

In many industrial applications it is necessary to determine the concentration of one or more elements in a bulk material. Often it is necessary or at least desired to determine said concentration in an online measurement. For example it is a well known problem that the total ash content in coal needs to be measured. Here, the total ash content is typically in the range of 1 to 50 percent. There are established techniques how to perform a measurement in order to determine the total ash content. The most common method is the so-called dual energy method. The sample is irradiated with two X-ray or gamma ray beams of different energy. The transmission is measured and the area weight and the average atomic number are determined. If the composition of the ash is known, one can calculate the ash content of the coal. In a more sophisticated method the surface of the coal is irradiated with an X-ray beam and the fluorescence peaks of the metals constituting the ash are measured (so called XRF measurement). With this method not only the total ash content but also the composition of the ash can be determined. Because of the higher energies of the fluorescence peaks of heavier elements the measurement of heavier elements is easier than the measurement of light elements.

Especially because of strict environment regulations it is not only necessary to determine the total ash content of coal but also the precise content of some poisonous elements, especially mercury. Because mercury is a heavy element with a charactaristic $K_\alpha$-line of high energy, the measurement of mercury would basically be easy with the above mentioned XRF technique. But it turned out that because of the very low mercury concentration of real-life samples, the results of online measurements using XRF technique are not satisfactory.

It is an object of this invention to provide a method for determining the concentration of an element in a material that can be performed as an online measurement and that makes it possible to precisely determine even very low concentrations, especially below 0.1%.

According to the invention, not the characteristic emission of the element of to interest is measured, but the characteristic absorption. This measurement takes advantage of the fact that the absorption of an element significantly rises when the energy of the irradiating beam goes beyond an characteristic absorption edge of the element. So, according to the invention, the difference between the intensity of the transmitted X-ray beam in an energy interval above the absorption edge and in an energy interval below the absorption edge is determined. This difference is in many applications directly linear to the concentration of the searched element over a large scale. In many applications, especially if the concentration of the searched element is low and if the searched element is a high Z element and the bulk material is a low Z material, the measurement of the absorption resulting from excitation has many advantages in relation to the measurement of the charactaristic emission. One of the most important aspects is that the relevant signals increase to a large extend in a linear manner with the thickness of the irradiated sample. So, one can enhance the measurement by using thicker layers of bulk material as long as the absorption of the material in the used energy range is low enough such that the bulk material is penetrated by the radiation such that the radiation can be detected by the detector. This is not at all the case when measuring the fluorescence, due to geometrical reasons.

Usually it will be necessary to keep the thickness of the sample constant or to measure the thickness or the area weight of the sample in order to take the thickness into account, when determining the concentration of the searched element.

Figure 2:
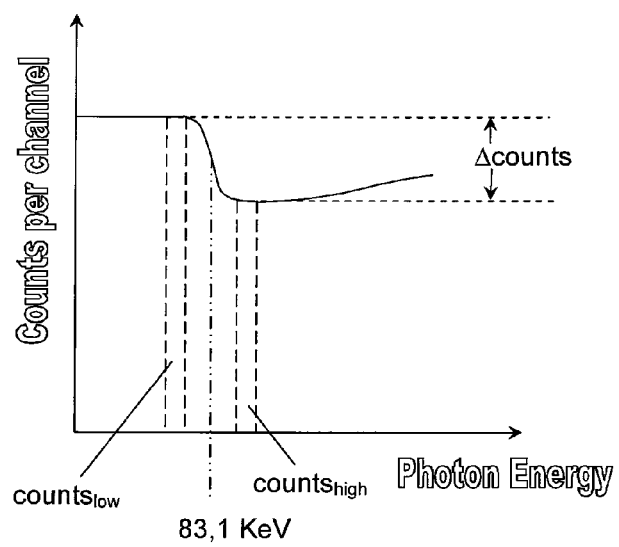
Figure 3:
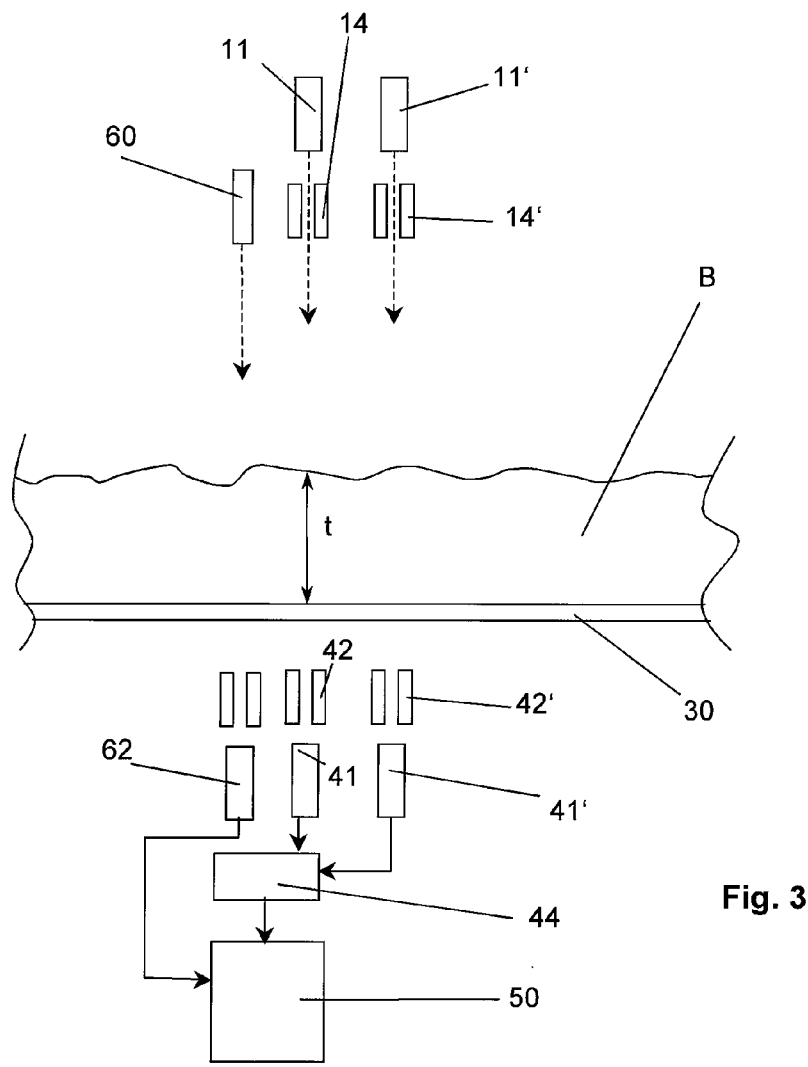
Figure 4:
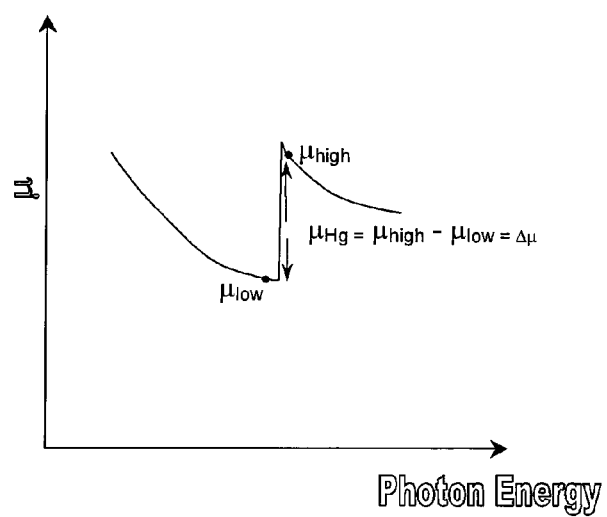
Figure 5:
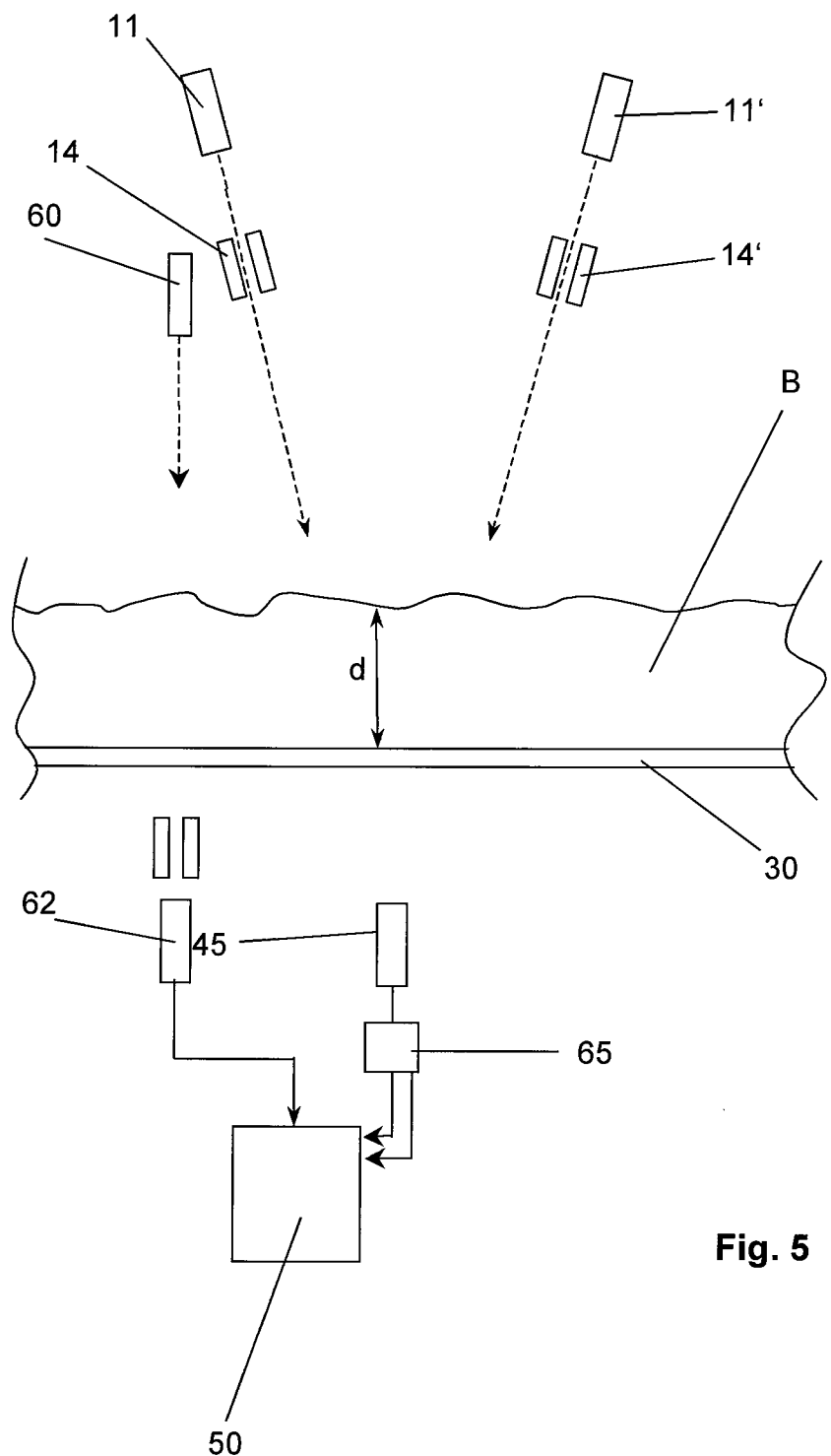
Figure 6:
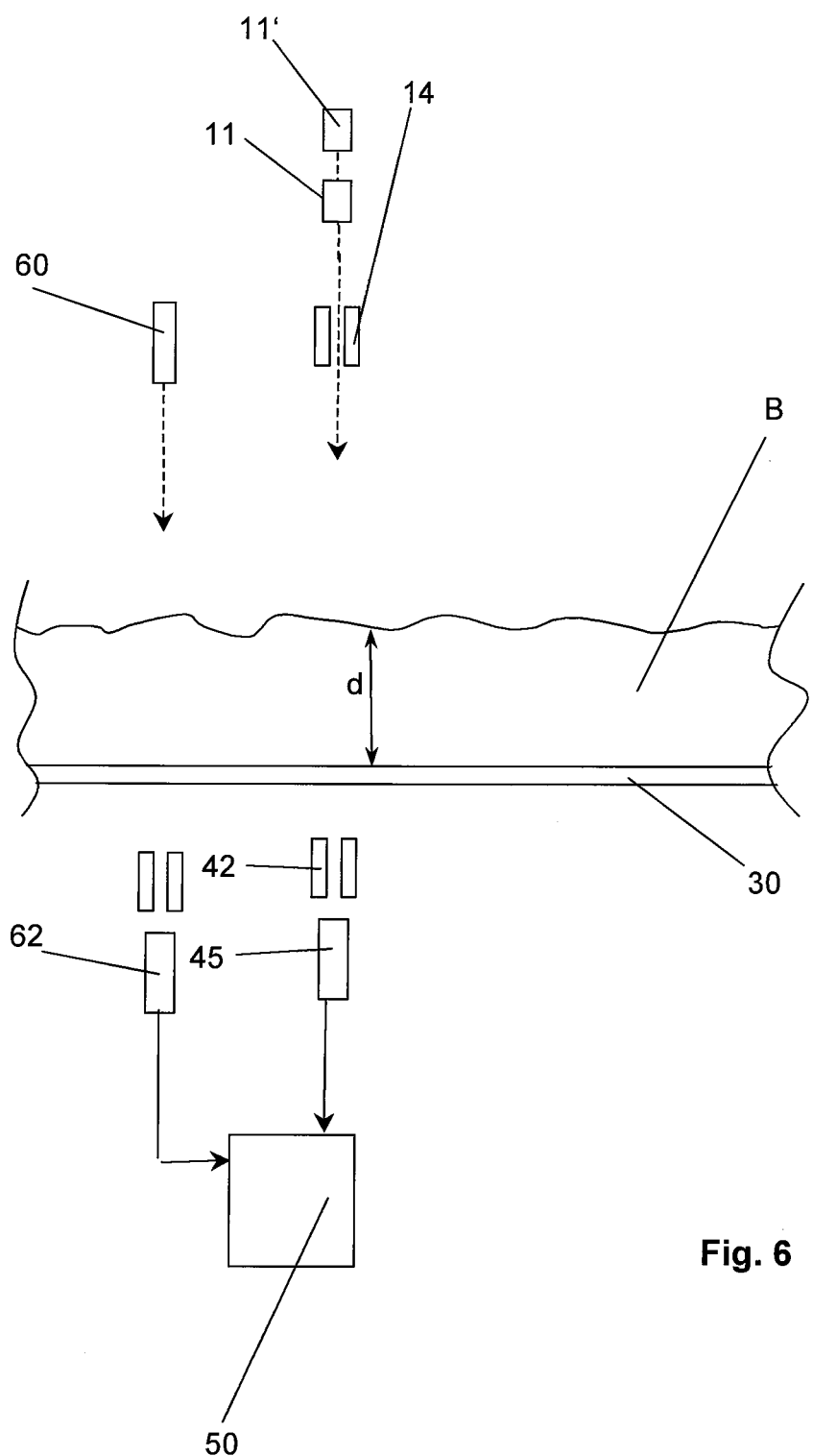

The invention will now be explained in detail in view of preferred embodiments with reference to the accompanying figures. The figures show:

FIG. 1 a diagrammatic representation of a first embodiment of the invention,

FIG. 2 a typical spectrum used for determining the concentration of mercury in coal with the photon energy on the X-axis and the counts on the Y-axis, FIG. 3 a diagrammatic representation of a second embodiment of the invention, FIG. 4 a typical spectrum as in FIG. 2 but with the absorption-coefficient on the Y-axis, FIG. 5 a variation of the second embodiment, and FIG. 6 a further variation of the second embodiment.

The invention will now be explained in detail. In the examples described the content of mercury in coal is determined. This is an important application of the invention but it needs to be mentioned that a lot other applications are possible. Especially if traces of a high-Z element, such as mercury, lead, uranium, plutonium, tungsten, gold etc. are to be measured in a bulk material with relatively low-Z average, such as coke, coal, petroleum, wood, ore, e.g. iron ore, and other low-Z minerals, etc. the method is very useful.

FIG. 1 shows all essential parts of a first embodiment of an apparatus for carrying out the method according to the invention. This apparatus comprises the following elements: An X-ray source 10, a first collimator 14 downstream of the X-ray source 10, a second collimator 42 downstream of the first collimator 14, an energy dispersive detector 40, a multichannel analyzer 44 connected to the energy dispersive detector and a computing unit 50 connected to the multi-channel analyzer. The X-ray source, the first collimator, the second collimator and the energy dispersive detector are collinear in respect to each other. A filter 12 might be provided downstream of the X-ray source. The atomic number of the filter material should be higher by two or three elements than the searched element. For Mercury a lead filter can be used. A conveyor belt 30 for conveying the bulk material B—here coal—is provided between the two collimators. The conveyor, especially a conveyor belt, preferably extends perpendicular to the X-ray beam propagating from the X-ray source to the X-ray detector. A means for measuring the area weight and/or the thickness of the bulk material on the conveyor is provided. This means can be in form of a $CS^{137}$ transmission line consisting of a $CS^{137}$ source and a detector (as will be described later). If the density of the material is constant, the layer-thickness t can be measured. A means for measuring the layer-thickness can be a laser scanner 20, but other measuring means are also possible. The means for measuring the thickness of the bulk material is also connected to the computing unit 50.

Since Compton- and/or Rayleigh scattered radiation might influence the measurement, especially due to an imperfect collimating, an additional detector 70 can be provided. In the embodiment shown this detector is arranged in a backscatter geometry, but it would also be possible to arrange the same in a transmission geometry. The signals of the additional detector 70 are transmitted to the computing unit 50, such that the measured scattered radiation can be used for correction purposes.

The X-ray source generates a continuum around the K-absorption edge of mercury at 83.1 KeV, for example between 70 and 90 KeV. All other energies can be filtered, since they are of no use for this measurement.

A typical spectrum that is "seen" by the detector, analyzed by the multi-channel analyzer and used by the computing unit to compute the desired information is shown in FIG. 2. One can clearly see the absorption edge at 83.1 keV. At this energy the transmission drops in a sharp step due to the change of the absorption at the absorption edge. The "height" of this step (later referred to as Δcounts) is directly proportional to the thickness of the material and to the concentration of the element of interest (here mercury), as long as a linear approximation is applicable. Such a linear approximation is in this example applicable for a thickness of the bulk material up to at least 5 Inches and for concentrations of mercury up to at least 0.1%. It goes without saying that the method described here is also applicable in the non-linear range; the non-linear formula will be given later. But in order to explain the invention by means of simple mathematics, the linear approximation is used in the following:

In a first energy interval just below the absorption edge the photons are counted in a defined time interval. The energy interval depends on the energy resolution of the detector system and is not rather critical, for example 5 keV. The time interval should be long enough to reduce the statistical error sufficiently, for example 30 s. The number of photons counted is referred to as $counts_{low}$. Respectively photons are counted just above the absorption edge in a second energy interval with the same width as the first energy interval. The time interval is of course identical to the time interval of the first energy interval. The number of photons counted is referred to as $counts_{high}$. As long as the element searched (here: mercury) is not present in the bulk material, $counts_{low}$ and $counts_{high}$ are basically identical. This changes when the element searched is present. In this case $counts_{high}$ is less than $counts_{low}$. The difference is referred to as Δcounts.

In linear approximation, the following mathematics apply:

$$\Delta counts = counts_{low} - counts_{high}$$

and $$counts_{high} = counts_{low} * c * d * const$$

with c=concentration of the element searched
d=thickness of the bulk material
const=constant (depending on the cross section of the resonant absorption, on the geometry and on the unit in which the concentration is computed)
so, $$\Delta counts = counts_{low} - counts_{low} * c * d \cdot const$$

and $$c = \frac{counts_{low} - \Delta counts}{counts_{low} * const * d}$$

The non-linear and thus more precise mathematics are given later in view of the second embodiment in terms of absorption coefficients.

It is an important advantage that (as long as one has a perfect collimation) the distance between the X-ray source 10 and the energy dispersive detector 50 is of no relevance. So, the X-ray source can be quite far remote from the conveyor.

FIG. 3 shows a second embodiment of the invention. Here, the bulk material is not irradiated with X-rays having a continuum around the absorption edge of the searched element, but with two distinct X- or gamma-rays with a small energy width (peak) each. For example the first X- or gamma-ray has an energy slightly below the absorption edge and the second gamma-ray has an energy slightly above the absorption edge. When using X-rays, the use of filters or monochromators will in general be necessary. A separate detector 41, 41' is assigned to each beam. Also a combination of a nuclear source and an X-ray tube is possible.

In the embodiment shown in FIG. 3 two gamma-ray sources are used, namely an Am-241 source 11 at 59.5 keV for the energy below the absorption edge and a Cd-109 source 11' at 88 keV KeV above the absorption edge. The first detector 41 is assigned to the Am-source 11 and the second detector 41' is assigned to the Cd-source 11'. Collimators 14, 14'; 42, 42' are used as in the first embodiment. An alternative for the low energy source could be Ba133 (80 keV). Alternatives for the high energy source could be Co57, EU155, EU152, or EU154.

As can be seen from FIG. 3, filters 12, 12a, 12b, and 12c can be used, both, on the source-side and on the detector side. On the source-side the filters 12, 12a improve the monochromatic nature of the incident beam, on the detector side the filters 12b, 12c help to eliminate scattered radiation (in this case together with the collimators 42, 42').

In this second embodiment not the thickness d of the bulk material is measured, but the area weight of the bulk material. This leads to more precise results if the density of the material is not constant. This measurement is performed as is known in the art by a high energy transmission measurement using a Cs-137 source 60 and a respective detector 62. This measurement of the area density could also be used in the first embodiment instead of the measurement of the thickness of the bulk material via a laser scanner.

The advantage in respect to the first embodiment is that the detectors do not need to be energy dispersive and that no multi-channel analyzer is necessary.

The mathematics are as follows:

First, the well-known general formula applies:

$$I = I_0 * e^{-\mu * \rho * d} \qquad (1)$$

with $I_o$=incident energy
I=measured energy
μ=absorption coefficient so, $$-\mu_{high} * \rho * d = \ln\left(\frac{I}{I_0}\right)_{high}$$

and $$-\mu_{low} * \rho * d = \ln\left(\frac{I}{I_0}\right)_{low}$$

and for the measurement with the Cs-source as can be seen from FIG. 4

$$\mu_{HG} = \mu_{high} - \mu_{low}$$

this leads to $$\mu_{HG} = \mu_{Cs} \frac{\ln\left(\frac{I}{I_0}\right)_{high} - \ln\left(\frac{I}{I_0}\right)_{low}}{\ln\left(\frac{I}{I_0}\right)_{Cs}}$$

FIG. 5 shows a variation of what is shown in FIG. 4. Here, a common detector 45 and a discriminator 65 are used. The Am-241 source 11 and the Cd-109 source 11' point towards this common detector 45 and the energies are separated by the discriminator 65.

FIG. 6 shows a variation of what is shown in FIG. 5. Here, the beam of the Cd-109 source 11' extends through the Am-241 source 11, so that both beams pass through the same area of the bulk material, which is to be preferred if the surface of the bulk material has not a uniform shape.

In order to further refine the measurement a measurement of the moisture of the bulk material can be measured, especially via a microwave measurement. Such a measurement can be performed in all described embodiments.

Finally it should be noted that an additional detector 70 for measuring scattered radiation can be provided in all shown embodiments.

As has already been pointed out, the method according the invention is especially useful to determine the content of heavy trace elements in coal, coke, petroleum and petroleum derivates in an online measuring process. But it needs to be pointed out that the method can also be used for other problems such as detecting uranium or plutonium in cargo or to detect tungsten or lead in gold.

The invention claimed is:

1. A method for determining the concentration of an element in a material, comprising:
    irradiating the material with an X-ray beam having a continuum in the area of an absorption edge of the element to be measured;
    measuring the intensity of the transmitted X-ray beam with an energy dispersive sensor;
    determining the intensity of the transmitted X-ray beam in an energy interval above the absorption edge and in an energy interval below the absorption edge; and
    computing the concentration of the element based on said intensities.

2. The method according to claim 1, wherein the material is transported on a conveying device and the computing is performed via a calculating device such that the concentration of the element is determined automatically in an online process.

3. The method according to claim 1, wherein the atomic number of the element is higher than the mean atomic number of the material.

4. The method according to claim 3, wherein the material is coal, or a product refined from coal, or oil, or a product refined from oil.

5. The method according to claim 1, wherein the element is one of mercury, lead, uranium, plutonium, tungsten, or gold.

6. The method according to claim 1, wherein the concentration of the element in the material is 0.1% or less.

7. The method according to claim 1, wherein the area weight or the thickness of the irradiated material is measured.

8. The method according to claim 1, wherein scattered radiation is measured.

9. An apparatus for carrying out the method of claim 1, said apparatus comprising:
    an X-ray source;
    the energy dispersive sensor being an energy dispersive X-ray detector arranged in a collinear manner to the X-ray source;
    a discriminator or a multi-channel analyzer being connected to the X-ray detector; and
    an evaluating device being connected to the discriminator or multi-channel analyzer.

10. The method according to claim 1, wherein the method is carried out using an apparatus including:
    the energy dispersive sensor that is an X-ray detector; and
    a discriminator or a multi-channel analyzer being connected to the X-ray detector.

11. A method for determining the concentration of an element in a material comprising:
    irradiating the material with a first X-ray or gamma ray beam having an energy above an absorption edge of the element to be measured;
    irradiating the material with a second X-ray or gamma ray beam having an energy below an absorption edge of the element to be measured;
    measuring the intensities of the transmitted first and second X-ray or gamma ray beams, using a discriminator or a multi-channel connected to an X-ray detector;
    determining the difference between, or the ratio of, the intensity of the transmitted first X-ray or gamma ray beam and the intensity of second X-ray or gamma ray beam; and
    computing the concentration of the element based on said difference or ratio.

12. The method according to claim 11, wherein the material is transported on a conveying device and the computing is performed via a calculating device such that the concentration of the element is determined automatically in an online process.

13. The method according to claim 11, wherein the atomic number of the element is higher than the mean atomic number of the material.

14. The method according to claim 13, wherein the material is coal, or a product refined from coal, or oil, or a product refined from oil.

15. The method according to claim 11, wherein the element is one of mercury, lead, uranium, plutonium, tungsten, or gold.

16. The method according to claim 11, wherein the concentration of the element in the material is 0.1% or less.

17. The method according to claim 11, wherein the area weight or the thickness of the irradiated material is measured.

18. The method according to claim 11, wherein scattered radiation is measured.

* * * * *